United States Patent [19]

Tessier et al.

[11] Patent Number: 5,026,862
[45] Date of Patent: Jun. 25, 1991

[54] PROCESS FOR THE PREPARATION OF 1.R, CIS CYCLOPROPANE DI-CARBOXYLIC ACID DERIVATIVES

[75] Inventors: Jean Tessier, Vincennes; Jean-Pierre Demoute, Montreuil-sous-Bois, both of France

[73] Assignee: Roussel Uclaf, Paris, France

[21] Appl. No.: 416,718

[22] Filed: Oct. 3, 1989

Related U.S. Application Data

[63] Continuation of Ser. No. 120,868, Nov. 16, 1987, abandoned, which is a continuation of Ser. No. 808,845, Dec. 12, 1985, abandoned, which is a continuation of Ser. No. 491,013, May 3, 1983, abandoned.

[30] Foreign Application Priority Data

May 6, 1982 [FR] France ................................ 82 07870

[51] Int. Cl.$^5$ ................. C07C 69/743; C07C 69/593; C07C 69/52
[52] U.S. Cl. .................................... 560/124; 560/205; 560/223; 560/225; 556/426; 556/442; 549/416; 548/308; 548/473; 546/300; 546/301
[58] Field of Search ................ 546/301, 300; 548/308, 548/473; 549/416; 560/124, 205, 223, 225; 556/426, 442

[56] References Cited

U.S. PATENT DOCUMENTS 4,312,817 1/1982 Martel et al. ...................... 558/354

OTHER PUBLICATIONS

Breuer et al., Tetrahedron, vol. 34, No. 7, pp. 997–1002, Pergamon Press (1978).

Primary Examiner—Alan L. Rotman
Attorney, Agent, or Firm—Bierman and Muserlian

[57] ABSTRACT

A novel process for the preparation of compounds in all their possible isomeric forms of the formula

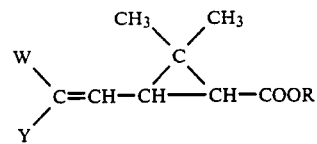

wherein R is selected from the group consisting of hydrogen, alkyl of 1 to 18 carbon atoms, an easily cleavable derivative of the alcohol R-OH and a residue of an alcohol used in the pyrethrinoid series and when Y is —COOR' or —COSR', W is hydrogen and W is halogen when Y is —COOR' and R' is selected from the group consisting of hydrogen, optionally unsaturated alkyl of 1 to 18 carbon atoms and optionally substituted with at least one functional group, aryl optionally substituted with at least one functional group and heterocycle optionally substituted with at least one functional group and when W is hydrogen, the double bond has Z configuration and when W is halogen, the double bond has the E configuration comprising reacting a compound of the formula

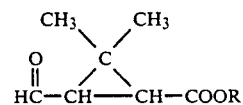

wherein R has the above definition with a compound of the formula

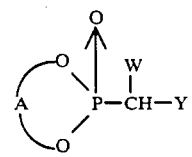

wherein W and Y have the above definitions and A is alkylene of 1 to 18 carbon atoms attached to the two oxygen atoms fixed on the phosphorus atom to obtain a compound of formula I with the double bond having the Z configuration when W is hydrogen and having the E configuration when W is halogen, the cyclopropane and the carboxyl of Y being in both cases in the cis position with respect to the double bond and novel intermediates.

5 Claims, No Drawings

PROCESS FOR THE PREPARATION OF 1.R, CIS CYCLOPROPANE DI-CARBOXYLIC ACID DERIVATIVES

PRIOR APPLICATION

This application is a continuation of U.S. patent application Ser. No. 120,868 filed Nov. 16, 1987 which is a continuation of U.S. patent application Ser. No. 808,845 filed Dec. 12, 1985 which is a continuation of U.S. patent application Ser. No. 491,013 filed May 3, 1983, all now abandoned.

STATE OF THE ART

Breuer et al [Tetrahedron, Vol. 34 (1978) p. 997 to 1002] describes the use of 2-carbethoxymethyl-4,5-dimethyl-2-oxo-1,3,2-dioxaphospholane, 2-cyanomethyl-4,5-dimethyl-2-oxo-1,3, 2-dioxaphospholane, 2-carbalkoxymethyl-5,5-dimethyl-2-oxo-1,3,2-phosphorinanes and 2-cyanomethyl-5,5-dimethyl-2-oxo-1, 3,2-dioxophosphorinane to react with aromatic and aliphatic aldehydes to form cis olefins. British patent No. 1,246,813 describes the preparation of trans pyrethric acid by the Wittig reaction.

OBJECTS OF THE INVENTION

It is an object of the invention to provide an improved process for the preparation of cyclopropane carboxylic acid derivatives of formula I.

It is another object of the invention to provide novel intermediates useful in the said process.

These and other objects and advantages of the invention will become obvious from the following detailed description.

THE INVENTION

The novel process of the invention for the preparation of compounds in all their possible isomeric forms of the formula

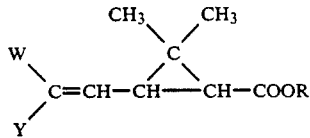

wherein R is selected from the group consisting of hydrogen, alkyl of 1 to 18 carbon atoms, an easily cleavable derivative of the alcohol R—OH and a residue of an alcohol used in the pyrethrinoid series and when Y is —COOR' or —COSR', W is hydrogen and W is halogen when Y is —COOR' and R' is selected from the group consisting of hydrogen, optionally unsaturated optionally cyclic, alkyl of 1 to 18 carbon atoms and optionally substituted with at least one functional group, aryl optionally substituted with at least one functional group and heterocycle optionally substituted with at least one functional group and when W is hydrogen, the double bond has Z configuration and when W is halogen, the double bond has the E configuration comprises reacting a compound of the formula

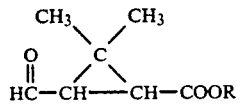

wherein R has the above definition with a compound of the formula

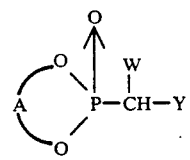

wherein W and Y have the above definitions and A is alkylene of 1 to 18 carbon atoms attached to the two oxygen atoms fixed on the phosphorus atom to obtain a compound of formula I with the double bond having the Z configuration when W is hydrogen and having the E configuration when W is halogen, the cyclopropane and the carboxyl of Y being in both cases in the cis position with respect to the double bond.

Examples of R' are saturated alkyls such as methyl, ethyl, isopropyl, propyl, n-butyl, sec.-butyl, isobutyl, n-pentyl, n-hexyl, tert.-butyl, tert.-pentyl and neopentyl; cycloalkyl such as cyclopropyl, cyclobutyl, cyclopentyl or cyclohexyl; cycloalkyl substituted with a lower alkyl such as 1-methylcyclobutyl, 1-methylcyclopentyl, 1-methylcyclohexyl or 2,2,3,3-tetramethylcyclopropyl; cycloalkylalkyl such as cyclopropylmethyl, cyclobutylmethyl, cyclopentylmethyl or cyclohexylmethyl; unsaturated alkyl such as vinyl, 1,1-dimethylallyl, acetylenic, ethynyl or propynyl.

Examples of R' substituted with one or more functional groups are preferably alkyl of 1 to 8 carbon atoms such as methyl, ethyl, propyl, isopropyl, n-butyl, isobutyl or tert.-butyl substituted with at least one member of the group consisting of halogen, —OH, —SH, —OR'$_1$ and —SR'$_1$ and R'$_1$ is selected from the group consisting of alkyl of 1 to 8 carbon atoms, —NO$_2$, —CN, —SO$_3$H, —PO$_4$H$_2$,

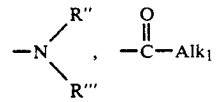

—SO$_2$Alk$_2$ and —SO Alk$_3$, R" and R''' are individually selected from the group consisting of hydrogen and alkyl of 1 to 8 carbon atoms and Alk$_1$, Alk$_2$ and Alk$_3$ are alkyl of 1 to 18 carbon atoms.

R' may also be alkyl substituted with an aryl group such as benzyl or phenethyl optionally substituted with at least one member of the group consisting of —OH, alkyl and alkoxy of 1 to 8 carbon atoms, —CF$_3$, —OCF$_3$, —SCF$_3$ and

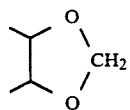

(G). R' may also be alkyl substituted on two adjacent carbon atoms with the group

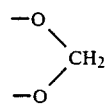

(G$_1$) or substituted with

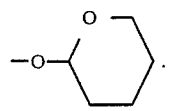

When R is an alkyl radical substituted by one or more functional groups, the preferred examples of R' are (1) —(CH$_2$)$_n$—CHal$_3$ wherein n is an integer from 1 to 8 and Hal is a halogen, such as —CH$_2$—CCl$_3$, —CH$_2$—CF$_3$, —CH$_2$—CH$_2$—CCl$_3$ or —CH$_2$—CH$_2$—CF$_3$, (2) —(CH$_2$)$_{n1}$—CHHal$_2$ wherein n$_1$ is 0 to 8 and Hal is halogen such as —CH$_2$—CHCl$_2$, —CH$_2$—CHF$_2$ and —CHF$_2$, (3) —(CH$_2$)$_n$—CH$_2$Hal wherein Hal and n have the above definitions, such as —CH$_2$—CH$_2$—Cl or —CH$_2$—CH$_2$F, (4) —C—(CHal$_3$)$_3$ wherein Hal is a halogen, such as —C(CF$_3$)$_3$ or

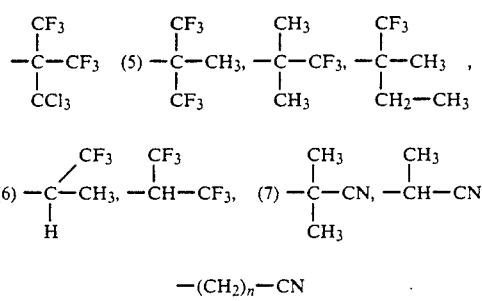

—(CH$_2$)$_n$—CN wherein n is 1 to 8, (8)

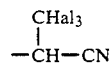

wherein Hal is a halogen, such as

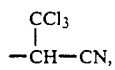 (9)

(CH$_2$)$_n$—OR$_a$ wherein n has the above definitions and R$_a$ is hydrogen or branched or linear alkyl of 1 to 8 carbon atoms such as —CH$_2$—OCH$_3$, —CH$_2$—CH$_2$—OCH$_3$, —CH$_2$—CH$_2$—O—CH$_2$—CH$_3$ or —CH$_2$—CH$_2$—OH, (10)

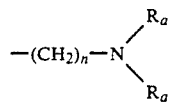

wherein n is 1 to 8 and both R$_a$ are individually hydrogen or branched or linear alkyl such as —CH$_2$—CH$_2$—NH—CH$_3$

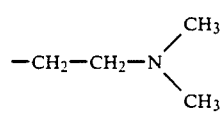

or

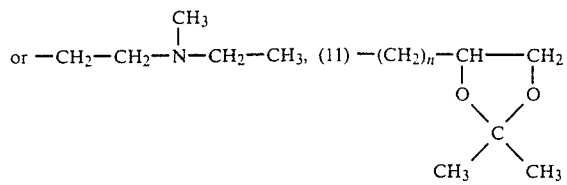

wherein n is 1 to 8 such as

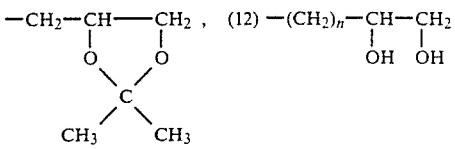

wherein n is 1 to 8 such as

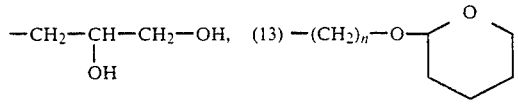

wherein n is 1 to 8 such as

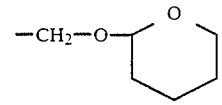

or

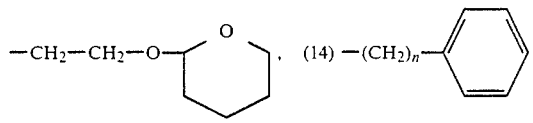

wherein n is 1 to 8 such as benzyl or phenethyl and (15)

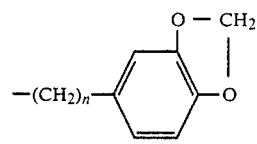

wherein n is 1 to 8 such as

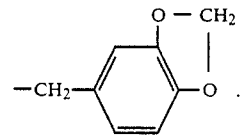

When R' is an optionally substituted aryl, preferred examples are phenyl optionally substituted with at least one member of the group consisting of —OH, alkyl and alkoxy of 1 to 8 carbon atoms, —CF$_3$, —OCF$_3$ and —SCF$_3$. Examples of R' as heterocycles are pyridinyl, furanyl, thiophenyl, oxazolyl and thiazolyl.

When W is a halogen, it may be chlorine or bromine but it is preferably fluorine. When R is alkyl, it is preferably methyl, ethyl or tert.-butyl. When R is an easily cleavable ester group up to 18 carbon atoms derived from R—OH, it is preferably tert.-butyl, —CH$_2$OCH$_3$, —CH$_2$—C$_6$H$_5$, —CH$_2$—SCH$_3$ or —Si(Alk)$_3$ where Alk is alkyl of 1 to 6 carbon atoms. When R is derived from an alcohol used in the pyrethrinoid field, it includes the alcohols used as intermediates and final biologically active esters.

In the process of the invention, the structure of the compounds of formula II with respect to the cyclopropane ring and the R group is the same as that of formula I which one desires to obtain without modification of the structure during the course of the reaction.

The compounds of formula I can exist in numerous isomeric forms due to the two asymetric carbon atoms in the 1- and 3-positions of the cyclopropane ring and other asymetric centers may be present in the Y and R substituents. The invention includes all possible isomers as well as mixtures thereof.

In a preferred mode of the invention, the compounds of formula I have a cyclopropane moiety with a 1R,cis or 1R, trans structure and most preferably 1R,cis structure.

In a preferred form of the invention, R is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

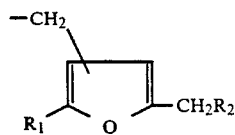
(3)

wherein R$_1$ is selected from the group consisting of hydrogen and methyl and R$_2$ is selected from the group consisting of —CH$_2$—C≡CH and monocyclic aryl,

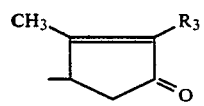
(4)

wherein R$_3$ is an aliphatic group of 2 to 6 carbon atoms containing at least one carbon-carbon unsaturation and especially selected from the group consisting of —CH$_2$—CH=CH$_2$, —CH$_2$—CH=CH—CH$_3$, —CH$_2$—CH=CH—CH$_2$—CH$_3$ and —CH$_2$—CH=CH—CH=CH$_2$.

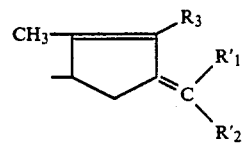

wherein R$_3$ has the above definition and R'$_1$ an dR'$_2$ are individually selected from the group consisting of hydrogen, halogen, alkyl of 1 to 6 carbon atoms, aryl of 6 to 10 carbon atoms, cyano and alkoxy carbonyl of 2 to 5 carbon atoms,

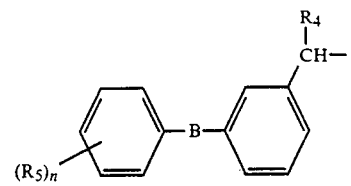
(6)

wherein B is selected from the group consisting of —CH$_2$—,

—O—, —S— sulfoxide and sulfone, R$_4$ is selected from the group consisting of hydrogen, C≡N, —CH$_3$, —CONH$_2$, —CSNH$_2$ and —C≡CH, n is an integer. from 0, 1 or 2 and R$_5$ is selected from the group consisting of halogen and —CH$_3$

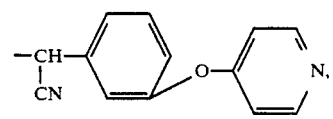
(7)

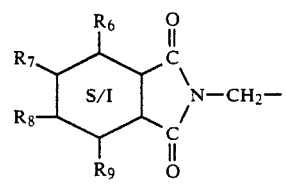
(8)

wherein R$_6$, R$_7$, R$_8$ and R$_9$ are selected from the group consisting of hydrogen, chlorine and methyl and S/I symbolizes an aromatic ring or dihydro or tetrahydro ring,

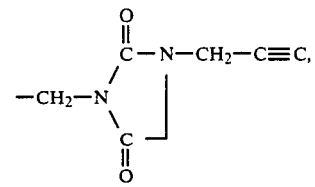
(9)

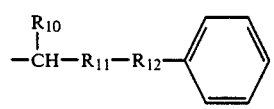
(10)

wherein R$_{10}$ is selected from the group consisting of hydrogen and —CN, R$_{12}$ is selected from the group consisting of —CH$_2$— and —O— and R$_{11}$ is selected from the group consisting of thiazolyl and thiadiazolyl with the bond to

being in any one of the positions, R$_{12}$ being bonded to R$_{11}$ by the carbon atom included between a sulfur atom and nitrogen atom,

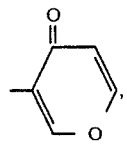 (11)

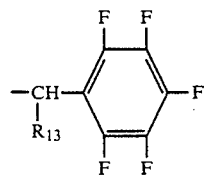 (12)

wherein $R_{13}$ is selected from the group consisting of hydrogen and —CN,

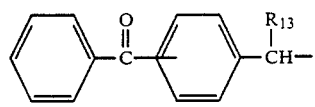 (13)

wherein $R_{13}$ has the above definition and the benzoyl is in the 3- or 4-position,

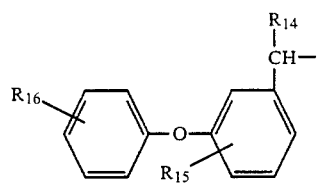 (14)

wherein $R_{14}$ is selected from the group consisting of hydrogen, methyl, ethynyl and —CN and $R_{15}$ and $R_{16}$ are individually selected from the group consisting of hydrogen, bromine and fluorine and (15)

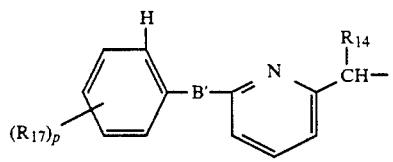 (15)

wherein $R_{14}$ has the above definition, p is 0, 1 or 2, each $R_{17}$ is selected from the group consisting of hydrogen of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, bromine and fluorine and B' is selected from the group consisting of —O— and —S—.

More preferably, R is selected from the group consisting of

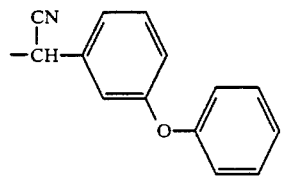

R also may preferably be selected from the group consisting of hydrogen and an easily cleavable group containing up to 18 carbon atoms, especially tert.-butyl, —CH$_2$OCH$_3$, —CH$_2$C$_6$H$_5$, —CH$_2$SCH$_3$ and Si(Alk)$_3$ and Alk is alkyl of 1 to 6 carbon atoms.

In a preferred mode of the process of the invention, the compound of formula III has the formula

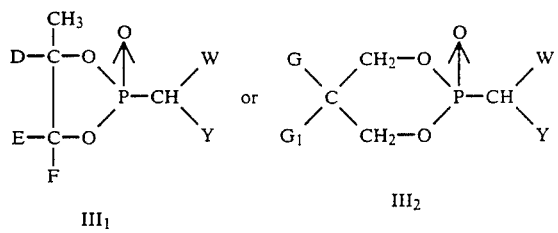

III$_1$        III$_2$ wherein C, D, E, F, G and G$_1$ are selected from the group consisting of hydrogen and alkyl of 1 to 3 carbon atoms and especially preferred are the compounds of formula III$_1$ wherein C and E are hydrogen and D and F are methyl.

Preferably, the reaction of the compounds of formulae II and III is effected in the presence of a strong base such as sodium hydride, alkali metal alcoholates, alkaline earth metal alcoholates, alkali metal amides and organolithium derivatives. The reaction is effect at temperatures of −70° to +25° C.

Examples of suitable solvents for the reaction are tetrahydrofuran, dimethylformamide, dimethylsulfoxide, hexamethylphosphorotriamide and dimethoxyethane and mixtures thereof with aliphatic or aromatic hydrocarbons.

In a preferred mode of the process of the invention, a compound of formula II is reacted with a compound of the formula

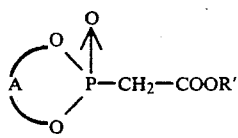   III$_A$ wherein A and R' have the above definition to obtain a compound of the formula

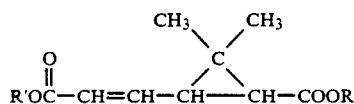   I$_A$ with the double bond having the Z configuration or reacting a compound of formula II with a compound of the formula

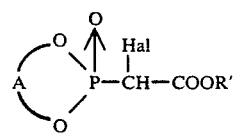   III$_B$ wherein A R' and Hal have the above definitions to obtain a compound of the formula

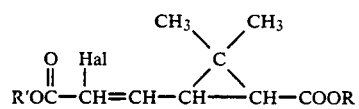   I$_B$ wherein the double bond has the E configuration.

Another preferred mode of the process of the invention comprises reacting a compound of formula II with a compound of the formula

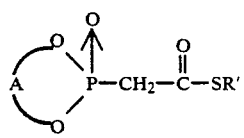   III$_C$ to obtain a compound of the formula

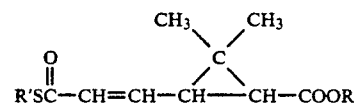   I$_C$ wherein the double bond has the Z configuration.

The starting materials of formula II can occur in cis, trans, racemic or optically active isomeric forms. When the compounds of formula II have the cis form and R is hydrogen, it may occur in the form of a lactone, namely the lactone of cis 2,2-dimethyl-3-dihydroxymethyl-cyclopropane-1-carboxylic acid.

The compounds of formula I are known chemical compounds having very interesting pesticidal properties or are useful as intermediates for the synthesis of very interesting pesticidal products. The compounds are described, for instance, in published Europe patent application No. 0038271, No. 0041021, No. 0048186 and No. 0050534. The compounds of formula I wherein Y is —COSR' are prepared by reacting a compound of the formula

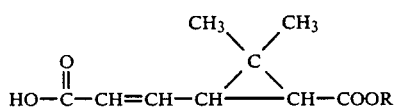

with a mercaptan of the formula R'SH.

The products of formula I are particularly useful as very interesting acaricides and insecticides or are useful to form compounds which have the said properties.

The process of the invention has the advantages of being simple and rapid, using easily accessible starting materials and results in compounds of formula I with the desired configuration, that is the compounds wherein the cyclopropane and the carboxyl of Y are cis with respect to the double bond.

The prior art processes for the preparation of the compounds of formula I do not permit the preparation of compounds of formula I except by a long synthesis or under conditions are not leading to the same stereospecificity. For example, European patent application Ser. No. 0048186 describes a process for the preparation of esters of the formula

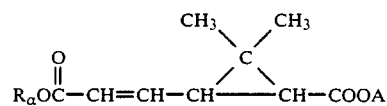

wherein R$_\alpha$ is alkyl or cyclic and A is an alcohol residue used in pyrethrinoid synthesis as well as the free acids and alkyl esters thereof by reacting a compound of the formula

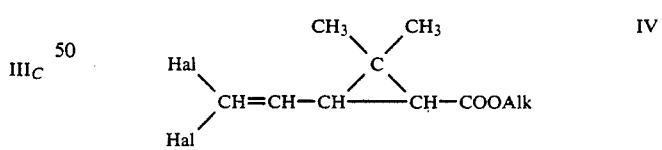   IV wherein Hal is a halogen and Alk is alkyl of 1 to 20 carbon atoms with an alkaline agent capable of attacking the halogen atoms and then in a second step either with an agent capable of introducing a carboxyl group to obtain a compound of the formula

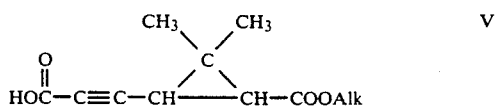   V and reacting the latter with an esterification agent of R$_\alpha$OH to obtain a compound of the formula

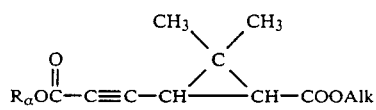

or with a compound of the formula $R_\alpha$—COOHal wherein Hal is halogen to obtain directly a compound of formula VI and reacting the compound of formula VI with a careful hydrogenation agent to obtain a compound of the formula

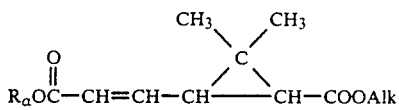

with the double bond having Z geometry which is then reacted with an acid hydrolysis agent capable of selectively cleaving the ester group in the 1-position to obtain a compound of the formula

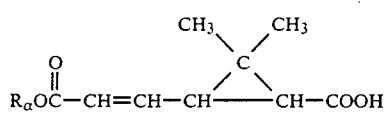

and reacting the latter with an alcohol of the formula AOH to obtain the corresponding ester of the formula

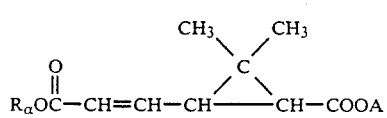

It is also known to prepare the compounds of formula I by reacting in an organic solvent a compound of the formula

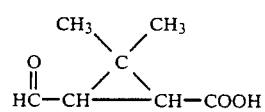

with a compound of the formula

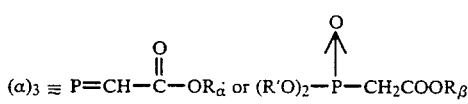

wherein $R_\alpha$ and $R_\beta$ are hydrocarbons by the classical Wittig reaction to obtain a compound of the formula

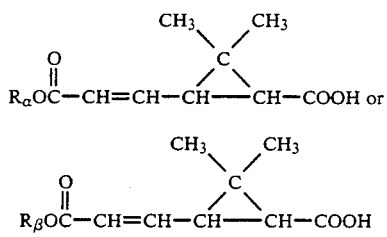

in the form of a mixture of E and Z isomers which must then be separated into the individual isomers. The said process is not commercially interesting since it leads to mixtures containing mainly products of E configuration which are the lesser interesting from the pesticidal view point.

The process of the invention which uses cyclic phosphonates leads to a rapid and simple process to obtain compounds of the desired configuration, namely the cyclopropane and the carboxyl ar cis with respect to the double bond.

Some of the products of formula III are known and they may be prepared, for example, by the reaction scheme

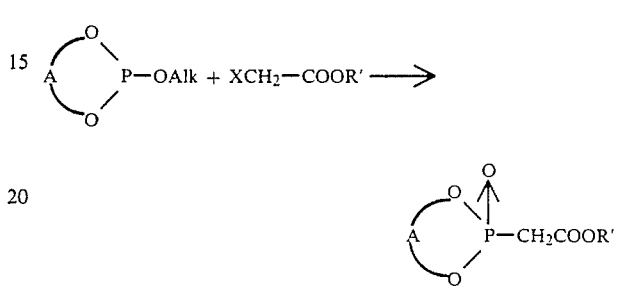

wherein X is halogen and Alk is lower alkyl.

Certain compounds of formula $III_A$ are novel such as compounds of the formula

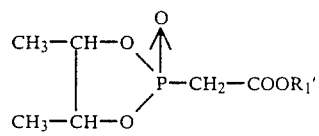

and

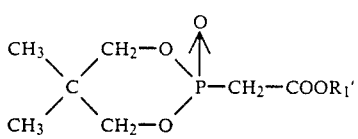

wherein $R'_1$ is propyl, isopropyl or tert.-butyl and are a part of the invention. The compounds of formulae $III_B$ and $III_C$ are also novel and are an object of the invention. Especially preferred compounds of formulae $III_B$ and $III_C$ are the compounds of the formulae

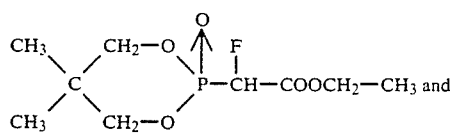

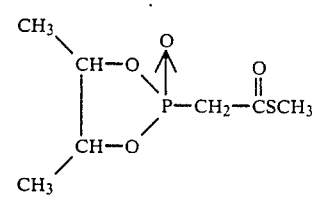

In the following examples there are described several preferred embodiments to illustrate the invention. However, it is to be understood that the invention is not intended to be limited to the specific embodiments.

EXAMPLE 1

(1R,cis,ΔZ)
2,2-dimethyl-3-[3-oxo-3-tert-butoxy-1-propenyl]-cyclopropane-carboxylic acid

STEP A:
2-tert.-butoxycarbonylmethyl-4,5-dimethyl-2-oxo-1,3,2-dioxaphospholane A mixture of 300 g of trimethyl phosphite and 200 ml of 2,3-butanediol was heated to 100° C. and the methanol formed was distilled off to obtain 170 g of 2-methoxy-4,5-dimethyl-1,3,2-dioxaphospholane with a boiling point of 66° C. at 20 mm Hg, 37 g of the said product were added over two hours to 62.5 g of tert.-butyl bromoacetate heated to 115° C. under reduced pressure of 140 mm Hg and the volatile products were removed under reduced pressure to obtain 59 g of 2-tert.-butoxycarbonylmethyl-4,5-dimethyl-2-oxo-1,3,2-dioxaphospholane which slowly crystallized.

NMR Spectrum (deuterochloroform): Peaks at 1.5 ppm (hydrogens of methyls of tert.-butyl); at 1.31 to 1.46 ppm (hydrogens of —CH$_3$ of ring); at 2.98 to 3.28 ppm (hydrogens of methylene attached to P); at 4.22 to 5.11 ppm (hydrogen of —CH— of ring).

STEP B: (1R,cis,ΔZ)
2,2-dimethyl-3-[3-oxo-3-tert.butoxy-1-propenyl]-cyclopropane-carboxylic acid 18.3 ml of diisopropylamine, 50 g of the product of Step A and 19 g of the lactone of (1R,cis) 2,2-dimethyl-3-dihydroxymethyl-cyclopropane-1-carboxylic acid were added at −40° C. to a mixture of 65 g of lithium bromide in 600 ml of anhydrous tetrahydrofuran and then a solution of 45 g of potassium tert.butylate in 100 ml of tetrahydrofuran was slowly added thereto at −40° C. The mixture was stirred at −40° C. for one hour and was then poured into one liter of aqueous 1N hydrochloric acid. The mixture was extracted with isopropyl ether and the organic phase was washed with water, dried and evaporated to dryness under reduced pressure to obtain 32 g of product which was 93% of (1R,cisΔZ) 2,2-dimethyl-3-[3-oxo-3-tert.butoxy-1-propenyl]-cyclopropane-carboxylic acid.

EXAMPLE 1A (1R,cis,ΔZ)
2,2-dimethyl-3-[3-oxo-3-tert.butoxy-1-propenyl]-cyclopropane-carboxylic acid

STEP A:
2-tert.butoxycarbonylmethyl-5,5-dimethyl-2-oxo-1,3,2-phosphorinane 25.5 g of 2-methoxy-5,5-dimethyl-1,3,2-dioxaphosphorinane were added over two hours under reduced pressure of 130 mm Hg to 27 ml of tert.butyl bromoacetate heated to 115° C. and the mixture was held at 115° C. for 15 minutes after which the mixture was distilled under reduced pressure. The residue was crystallized from isopropyl ether to obtain 35 g of 2-tert.butoxycarbonylmethyl-5,5-dimethyl-2-oxo-1,3,2-phosphorinane melting at 98° C.

NMR Spectrum (deuterochloroform): Peaks at 1.49 ppm (hydrogens of methyls of tert.butyl); at 1.06 and 1.1 ppm (hydrogens of geminal methyls); at 2.8 and 3.16 ppm (hydrogens of —CH$_2$—α— to P); J$_{H-P}$=22 Hz.

STEP B: (1R,cis,ΔZ)
2,2-dimethyl-3-[3-oxo-3-tert.butoxy-1-propenyl]-cyclopropane-carboxylic acid Using the procedure of Step B of Example 1, the product of Step A was reacted to obtain (1R,cis,ΔZ) 2,2-dimethyl-3-[3-oxo-3-tert.butoxy-1-propenyl]-cyclopropane-carboxylic acid

EXAMPLE 2

Methoxymethyl (1R,cis,ΔZ)
2,2-dimethyl-3-[3-oxo-3-methoxy-1-propenyl]-cyclopropane-carboxylate

STEP A:
2-methoxycarbonylmethyl-4,5-dimethyl-2-oxo-1,3,2-dioxaphospholane 69.8 g of 2-methoxy-4,5-dimethyl-1,3,2-dioxaphospholane were added over 70 minutes to 45 ml of methyl 1-bromoacetate heated to 120°–130° C. and the mixture was cooled to room temperature. Excess methyl bromoacetate was distilled off and the raw product was rectified to obtain 73 g of 2-methoxycarbonylmethyl-4,5-dimethyl-2-oxo-1,3,2-dioxaphospholane boiling at 130°–132° C.

STEP B: Methoxymethyl (1R,cis)
2,2-dimethyl-3-formyl-cyclopropane-carboxylate 70 ml of acetyl chloride were added with stirring to a mixture of 90 ml of methylal and 2.4 ml of methanol and the mixture was allowed to stand for several hours to obtain chloromethyl methyl ether. 6.7 g of lithium hydride were added over 30 minutes at about 15°±2° C. to a solution of 110 g of the lactone of (1R,cis) 2,2-dimethyl-3-dihydroxymethyl-cyclopropane-carboxylic acid in 500 ml of tetrahydrofuran and after stirring the mixture for 30 minutes, the mixture containing chloroethyl methyl ether was added thereto. The mixture was stirred at 20° C. for four hours and was poured into aqueous sodium bircarbonate solution. The mixture was extracted with isopropyl ether and the organic phase was washed with water, dried and evaporated to dryness under reduced pressure to obtain 117 g of raw product which was distilled to obtain methoxymethyl (1R,cis) 2,2-dimethyl-3-formyl-cyclopropane-carboxylate with a boiling point of 65° to 70° C. at 5×10$^{-2}$ mm Hg.

STEP C: Methoxymethyl (1R,cis,ΔZ)
2,2-dimethyl-3-[3-oxo-3-methoxy-1-propenyl]-cyclopropane-carboxylate Using the procedure of Step B of Example 1, 1.9 g of the product of Step B and 2.7 g of the product of Step A were reacted to obtain 3 g of raw product containing 90% of methoxymethyl (1R,cis,ΔZ) 2,2-dimethyl-3-[3-oxo-3-methoxy-1-propenyl]-cyclopropane-carboxylate.

EXAMPLE 3

Methoxymethyl (1R,cis,ΔZ)
2,2-dimethyl-3-[3-oxo-3-ethoxy-1-propenyl]-cyclopropane-carboxylate Using the procedure of Step B of Example 1, 1.9 g of methoxymethyl (1R,cis) 2,2-dimethyl-3-formyl-cyclopropane -1-carboxylate and 3 g of 2-ethoxycarbonylmethyl-4,5-dimethyl -2-oxo-1,3,2-dioxaphospholane [prepared as described by Breuer et al. Tetrahedron, Vol. 34 (1973), p. 997] to obtain 1.6 g of a mixture consisting of 99.5% of methoxymethyl (1R,cis,ΔZ) 2,2-dimethyl-3-[3-oxo-3-ethoxy-1-propenyl]-cyclopropane-carboxylate melting at 100° C.

EXAMPLE 4

Tert.-butyl (1R,cis,ΔZ) 2,2-dimethyl-3-[3-oxo-3-methylthio-1-propenyl]-cyclopropane-carboxylate

STEP A: Methyl bromothioacetate 14 ml of pyridine and 15 ml of methyl mercaptan were added at 10° C. to 150 ml of benzene and after cooling the mixture to 0° C., a solution of 14 ml of bromoacetyl chloride in 50 ml of benzene was added thereto over 30 minutes. After allowing the temperature to rise to 20° C., the mixture was stirred at 20° C. for four hours and was poured into an iced N hydrochloric acid solution. The mixture was stirred for 15 minutes and the decanted benzene phase was dried and evaporated to dryness under reduced pressure to obtain a product which was rectified to obtain 20 g of methyl bromothioacetate with a boiling point of 36° C. at 0.05 mm Hg.

STEP B: 2-(methylthiocarbonylmethyl)-4,5-dimethyl-2-oxo-1,3,2-dioxaphospholane 18.7 g of the product of Step A was added dropwise over 30 minutes to 18.7 g of 2-methoxy-4,5-dimethyl-1,3,2-dioxaphospholane at 130° C. and the mixture was stirred at 140° C. for one hour and was then evaporated to dryness under reduced pressure at 80° C. to obtain 2.5 g of 2-(methylthiocarbonylmethyl)-4,5-dimethyl-2-oxo-1,3,2-dioxaphospholane.

STEP C: Tert.-butyl (1R,cis,ΔZ) 2,2-dimethyl-3-[3-oxo-3-methylthio-1-propenyl]-cyclopropane-carboxylate 45 ml of a solution of 2.3 M of butyllithium in cyclohexane were added with stirring at 0° to 5° C.. to a mixture of 9.73 g of diisopropylamine and 100 ml of tetrahydrofuran to form lithium diisopropylamide. The said mixture was added over 20 minutes at −50° C. under an inert atmosphere to a mixture of 19.6 g of 2-methylthiocarbonylmethyl-4,5-dimethyl-2-oxo-1,3,2-dioxaphospholane in 100 ml of tetrahydrofuran and the mixture was held at ≦−30° C.

The said product was added at −50° C. to a solution of 14 g of tert.-butyl (1R,cis) 2,2-dimethyl-3-formyl-cyclopropane-carboxylate in 200 ml of tetrahydrofuran and the mixture was stirred at −30° C. for 90 minutes and was then poured into aqueous saturated monosodium phosphate solution. The mixture was extracted with ethyl acetate and the organic phase was washed with water, dried and filtered. The filtrate was evaporated to dryness under reduced pressure and the 30 g of residue were chromatographed over silica gel. Elution with a 9-1 hexane-ethyl acetate mixture yielded 6.9 g of tert.-butyl (1R,cis,ΔZ) 2,2-dimethyl-3-[3-oxo-3-methylthio-1-propenyl]-cyclopropane-carboxylate melting at 57°–58° C.

EXAMPLE 5

(1R,cis,ΔE) 2,2-dimethyl-3-/2-fluoro 3-oxo-3-ethoxy-1-propenyl/cyclopropane-carboxylic acid

STEP A: 2-ethoxycarbonylfluoromethyl-5,5-dimethyl-2-oxo-1,3,2-dioxaphosphorinane A mixture of 10 g of ethyl bromofluoroacetate and 6.4 g of 2-methoxy-5,5-dimethyl-1,3,2-dioxaphosphorinane was heated at 150° C. under pressure of 500 mm Hg, for 3 hours and the mixture was cooled and chromatographed over silica gel. Elution with a 1-1-1 chloroform-acetone-hexane mixture resulted in a 30% yield of 2-ethoxycarbonylfluoromethyl-5,5-dimethyl-2-oxo-1,3,2-dioxaphosphorinane.

NMR Spectrum (deuterochloroform): Peaks at 0.91 and 1.3 ppm (hydrogens of methyls of ring); at 1.21–1.33–1.45 ppm and 4.18–4.3–4.41–4.52 ppm (hydrogens of —CH$_2$—CH$_3$ of ester); 3.66 to 4.5 ppm (hydrogens of CH$_2$O of ring); at 4.91–5.11 ppm and 5.7–5.9 ppm (hydrogens of —CH—α to F and P); $J_{H-P}=12$ Hz and $J_{H-f}=47$ Hz.

STEP B: (1R,cis,ΔE) 2,2-dimethyl-3-[2-fluoro 3-oxo-3-ethoxy-1-propenyl]-cyclopropane-carboxylic acid 0.2 ml of diisopropylamine, 0.25 g of the lactone of (1R,cis) 2,2-dimethyl-3-dihydroxymethyl-cyclopropane-carboxylic acid and 0.5 g of the product of Step A were added at −40° C. to a mixture of 0.5 g of lithium bromide in 10 ml of tetrahydrofuran and then a solution of 0.5 g of potassium tert.-butylate in 3 l of tetrahydrofuran was slowly added thereto at −40° C. The mixture was held at −40° C. for one hour and was then poured into dilute hydrochloric acid. The mixture was extracted with ethyl acetate and the organic phase was evaporated to dryness under reduced pressure to obtain a product consisting of 95% of (1R,cis,ΔE) 2,2-dimethyl-3-/2-fluoro 3-oxo-3-ethoxy-1-propenyl/-cyclopropane-carboxylic acid.

EXAMPLE 6

(1R,cis,ΔZ) 2,2-dimethyl-3-[3-oxo-3-methoxy-1-propenyl]-cyclopropane-carboxylic acid 2.84 g of the lactone of (R,cis) 2,2-dimethyl-3-dihydroxymethyl-cyclopropane-carboxylic acid were added at −10° C. to a mixture of 10 g of lithium bromide and 40 ml of anhydrous tetrahydrofuran and after cooling the mixture to −30° C., 4 ml of diisopropylamine were added thereto followed by 5.6 g of 2-methoxycarbonylmethyl-4,5-dimethyl-2-oxo-1,3,2-dioxaphospholane and finally a solution of 4.8 g of potassium tert.-butylate in 20 ml of tetrahydrofuran. The mixture stood at −30° C. for one hour and was then poured into 200 ml of ice and 1N hydrochloric acid. The mixture was vacuum filtered to obtain 2.34 g of crystalline product which was 99.5% of (1R,cis,ΔZ) 2,2-dimethyl-3-[3-oxo-3-methoxy-1-propenyl]-cyclopropane-carboxylic acid melting at 100° C.

EXAMPLE 7

(1R,cis,ΔZ)
2,2-dimethyl-3-[3-oxo-3-ethoxy-1-propenyl]-cyclopropane-carboxylic acid 1.420 g of the lactone of (1R,cis) 2,2-dimethyl-3-dihydroxymethyl-cyclopropane-carboxylic acid and 3 g of 2-ethoxycarbonylmethyl-4,5-dimethyl-2-oxo-1,3,2-dioxaphospholane were added to a mixture of 5 g of lithium bromide in 20 ml of tetrahydrofuran and then a solution of 2 ml of diisopropylamine in 10 l of tetrahydrofuran was added thereto at −20° C. followed by the addition of a solution of 2.5 g of potassium tert.-butylate in 10 ml of tetrahydrofuran at −30° to −35° C. The mixture was held at −30° C. for one hour and was poured into a mixture of ice-water concentrated hydrochloric acid. The mixture was filtered and the crystals were dried to obtain 1.51 g of product melting at 100° C. which was 98.9% of (1R,cis,ΔZ) 2,2-dimethyl-3-[3-oxo-3-ethoxy-1-propenyl]-cyclopropane-carboxylic acid.

EXAMPLE 8

(1R,cis,ΔZ)
2,2-dimethyl-3-[3-oxo-3-propoxycarbonyl-1-propenyl/-cyclopropane-carboxylic acid

STEP A:
2-propoxycarbonylmethyl-4,5-dimethyl-2-oxo-1,3,2-dioxaphospholane

Using the procedure of Step A of Example 1, 3.8 g of n-propyl bromoacetate and 2.42 g of 2-methoxy-4,5-dimethyl-1,3,2-dioxaphospholane were reacted to obtain 3.62 g of raw 2-propoxycarbonylmethyl-4,5-dimethyl-2-oxo-1,3,2-dioxaphospholane which was used as is for the next step.

STEP B: (1R,cis,ΔZ)
2,2-dimethyl-3-[3-oxo-3-propoxy-1-propenyl)-cyclopropane-carboxylic acid Using the procedure of Example 6, 1.26 g of the lactone of (1R,cis) 2,2-dimethyl-3-dihydroxymethyl-cyclopropane-carboxylic acid and 3.13 g of the product of Step A were reacted to obtain after crystallization from hexane 0.89 g of (1R,cis,ΔZ) 2,2-dimethyl-3-[3-oxo-3-propoxy-1-propenyl]-cyclopropane-carboxylic acid melting at 59° C. and having a specific rotation of $[\alpha]_D^{20} = +77° \pm 1.5°$ (c=1% in chloroform).

EXAMPLE 9

(1R,cis,ΔZ)
2,2-dimethyl-3-[3-oxo-3-isopropoxy-1-propenyl]-cyclopropane-carboxylic acid

STEP A:
2-isopropoxycarbonylmethyl-4,5-dimethyl-2-oxo-1,3,2-dioxaphospholane Using the procedure of Step A of Example 1, 2.03 g of isopropyl bromoacetate and 1.3 g of 2-methoxy-4,5-dimethyl-1,3,2-dioxaphospholane were reacted to obtain 1.94 g of raw 2-isopropoxycarbonylmethyl-4,5-dimethyl-2-oxo-1,3,2-dioxaphospholane used as is for the next step.

STEP B: (1R,cis,ΔZ)
2,2-dimethyl-3-[3-oxo-3-isopropoxy-1-propenyl]-cyclopropane-carboxylic acid Using the procedure of Example 6, 0.76 g of the lactone of (1R,cis) 2,2-dimethyl-3-dihydroxymethyl-cyclopropane-carboxylic acid and 1.9 g of 2-isopropoxycarbonylmethyl-4,5-dimethyl-2-oxo-1,3,2-dioxaphospholane were reacted to obtain 1 of (1R,cis,ΔZ) 2,2-dimethyl-3-[3-oxo-3-isopropoxy-1-propenyl]-cyclopropane-carboxylic acid melting at 100° C. and having a specific rotation of $[\alpha]_D^{20} = +71° \pm 2°$ (c=1% in chloroform) and 0.09 g of the corresponding E isomer.

EXAMPLE 10

Methoxymethyl (1R,cis,ΔZ)
2,2-dimethyl-3-[3-oxo-3-tert.butoxy-1-propenyl]-cyclopropane-carboxylate Using the procedure of Step B of Example 1, 3.25 g of 2-tert.-butoxycarbonylmethyl-4,5-dimethyl-2-oxo-1,3,2-dioxaphospholane and 1.5 g of methoxymethyl (1R,cis) 2,2-dimethyl-3-formyl-cyclopropane-carboxylate were reacted to obtain after chromatography over silica gel and elution with a 9-1 hexane-ethyl acetate mixture 1.9 g of methoxymethyl (1R,cis,ΔZ) 2,2-dimethyl-3-[3-oxo-3-tert.-butoxy-1-propenyl]-cyclopropane-carboxylate melting at <50° C. and 0.1 g of the corresponding E isomer.

EXAMPLE 11

Tert.-butyl (1R,cis,ΔZ)
2,2-dimethyl-2-[3-oxo-3-methoxy-1-propenyl]-cyclopropane-carboxylate 1.3 ml of a solution of 2M butyllithium in cyclohexane were added at −10° to −20° C. to a mixture of 0.4 ml of diisopropylamine and 4 ml of tetrahydrofuran and the mixture was stirred at −10° to −20° C. for 15 minutes and was then cooled to −50° to −60° C. The mixture was poured into a mixture of 0.4 g of tert.-butyl (1R,cis) 2,2-dimethyl-3-formyl-cyclopropane-carboxylate, 0.562 g of 2-methoxycarbonylmethyl-4,5-dimethyl-2-oxo-1,3,2-dioxaphospholane and 10 ml of tetrahydrofuran cooled to −50° to −60° C. and the mixture was held at −40° C. for one hour and was then poured into an iced aqueous saturated monosodium phosphate solution. The mixture eas extracted with isopropyl ether and the organic phase was dried and evaporated to dryness to obtain 0.5 g of product of which was 88% of tert.-butyl (1R,cis,ΔZ) 2,2-dimethyl-3-[3-oxo-3-methoxy-1-propenyl]-cyclopropane-carboxylate.

EXAMPLE 12

(1R,trans,ΔZ)
2,2-dimethyl-3-[3-oxo-3-ethoxy-1-propenyl[-cyclopropane-carboxylic acid Using the procedure of Step B of Example 1, 2 g of (1R,trans) 2,2-dimethyl-3-formyl-cyclopropane-carboxylic acid and 4.1 g of 2-ethoxycarbonylmethyl-4,5-dimethyl-2-oxo-1,3,2-dioxaphospholane were reacted to obtain after chromatography over silica gel and elution with a 6-4 cyclohexane-ethyl acetate mixture containing 1% of acetic acid 1.73 g of product containing 75% of (1R,trans,ΔZ) 2,2-dimethyl-3-[3-oxo-3-ethoxy -1-propenyl]-cyclopropane-carboxylic acid.

EXAMPLE 13

(R,S)α-cyano-3-phenoxy-benzyl (1R,cis,ΔZ)
2,2-dimethyl-3-[3-oxo-3-ethoxy-1-propenyl]-cyclopropane-carboxylate A solution of 0.495 g of potassium tert.-butylate in 6 ml of tertrahydrofuran was slowly added at −60° C. to a mixture of 1 g of 2-ethoxycarbonylmethyl-4,5-dimethyl-2-oxo-1,3,2-dioxaphospholane and 10 ml of tetrahydrofuran and after 10 minutes at −60° C., the mixture was slowly poured into a mixture of 1.2 g of (R,S)α-cyano-3-phenoxy-benzyl (1R,cis) 2,2-dimethyl-3-formyl-cyclopropane-carboxylate in 13 ml of tetrahydrofuran. The mixture stood at −60° C. for 10 minutes and was then poured into a 1N hydrochloric acid solution. The mixture was extracted with methylene chloride and the organic phase was washed with water, dried and evaporated to dryness. The residue was chromatographed over silica gel and was eluted with a 8-2 hexane-ethyl acetate mixture to obtain 0.96 g of (R,S)α-cyano-3-phenoxy-benzyl (1R,cis,ΔZ) 2,2-dimethyl-3-[3-oxo-3-ethoxy-1-propenyl]-cyclopropane-carboxylate and after further chromatography 0.3 g of the E isomer.

EXAMPLE A (S)α-cyano-3-phenoxy-benzyl (1R,cis,ΔZ) 2,2-dimethyl-3-[3-oxo-3-methylthio-1-propenyl]-cyclopropane-carboxylate 2.16 g of dicyclohexylcarbodiimide were added at 0° C. to a mixture of 50 mg of 4-dimethylamino-pyridine, 4.1 g of (S)α-cyano-3-phenoxy-benzyl (1R,cis,ΔZ) 2,2-dimethyl-3-[3-oxo-3-hydroxy-1-propenyl]-cyclopropane-carboxylate and 20 ml of methylene chloride and after stirring the mixture for 5 minutes, a solution of 545 mg of methyl mercaptan in 5 ml of benzene was added thereto all at once. The mixture was stirred at 0° C. for 5 minutes and then at 20° C. for 16 hours and was vacuum filtered. The filtrate was washed with aqueous N hydrochloric acid, then with water and evaporated to dryness under reduced pressure. The residue was chromatographed over silica gel and was eluted with a 9-1 cyclohexane-ethyl acetate mixture to obtain 1.2 g of (S)α-cyano-3-phenoxy-benzyl (1R, cis,ΔZ) 2,2-dimethyl-3-[3-oxo-3-methylthio-1-propenyl]-cyclopropane-carboxylate melting at 87° C. and having a specific rotation of $[\alpha]_D^{20} = +51°$ (c=1% in benzene).

EXAMPLE B (S)α-cyano-3-phenoxy-benzyl (1R,cis,ΔZ) 2,2-dimethyl-3-[3-oxo-3-ethylthio-1-propenyl]-cyclopropane-carboxylate 1.5 ml of ethane thiol was added all at once to a solution of 2 g of (S)α-cyano-3-phenoxy-benzyl (1R,cis,ΔZ) 2,2-dimethyl-3-[3-oxo-3-hydroxy-1-propenyl]-cyclopropanecarboxylate in 10 ml of methylene chloride and then a solution of 1 g of dicyclohexylcarbodiimide, 40 mg of 4-dimethylaminopyridine and 5 ml of methylene chloride were added thereto at 5° C. The mixture was stirred at 5° C. for 5 minutes and at room temperature for three hours and was then filtered. The filtrate was evaporated to dryness under reduced pressure and the residue was chromatographed over silica gel. Elution with an 8-2 n-hexane-ethyl acetate mixture yielded 1.2 g of (S)α-cyano-3-phenoxy-benzyl (1R,cis,ΔZ) 2,2-dimethyl-3-[3-oxo-3-ethylthio-1-propenyl]-cyclopropane-carboxylate melting at 47° C. and having a specific rotation of $[\alpha]_D^{20} = +59°$ (C=0.4% in chloroform).

EXAMPLE C (S)α-cyano-3-phenoxy-benzyl (1R,cis,ΔZ) 2,2-dimethyl-3-[3-oxo-3-isopropylthio-1-propenyl]-cyclopropane-carboxylate 3 ml of 2-propanethiol were added all at once to a solution of 3.9 g of (S)α-cyano-3-phenoxy-benzyl (1R,cis,ΔZ) 2,2-dimethyl-3-[3-oxo-3-hydroxy-1-propenyl]-cyclopropane-carboxylate in 25 ml of methylene chloride and then a solution of 2 g of dicyclohexylcarbodiimide, 70 mg of 4-dimethylaminopyridine and 10 ml of methylene chloride was added thereto at 5° C. The mixture was stirred at 5° C. for five minutes and at room temperature for three hours and was filtered. The filtrate was evaporated to dryness under reduced pressure and the residue was chromatographed over silica gel. Elution with an 85-15 n-hexane-ethyl acetate mixture yielded 3.1 g of (S) α-cyano-3-phenoxy-benzyl (1R,cis,ΔZ) 2,2-dimethyl-3-[3-oxo-3-isopropylthio-1-propenyl]-cyclopropane-carboxylate melting at 80° C. and having a specific rotation of $[\alpha]_D^{20} = +69°$ (c=0.5% in chloroform).

EXAMPLE D (S)α-cyano-3-phenoxy-benzyl (1R,cis,ΔZ) 2,2-dimethyl-3-[3-oxo-3-tert.butylthio-1-propenyl]-cyclopropane-carboxylate 150 mg of 4-dimethylamino-pyridine and 1.9 g of dicyclohexylcarbodiimide were added at 5° C. to a solution of 3.46 g of (S)α-cyano-3-phenoxy-benzyl (1R,cis,ΔZ) 2,2-dimethyl-3-[3-oxo-3-hydroxy-1-propenyl]-cyclopropane-carboxylate in 20 ml of methylene chloride and after stirring the mixture at 5° C. for 5 minutes, 5 ml of tert.-butylmercaptan were added thereto. The mixture was stirred at 5° C. for 5 minutes and at 20° C. for three hours and was filtered. The filtrate was evaporated to dryness under reduced pressure and the residue was chromatographed over silica gel. Elution with a 9-1 cyclohexane-ethyl acetate mixture yielded 1.4 g of (S)α-cyano-3-phenoxy-benzyl (1R,cis,ΔZ) 2,2-dimethyl-3-[3-oxo-3-tert.butylthio-1-propenyl]-cyclopropane-carboxylate melting at 76° C. and having a specific rotation of $[\alpha]_D^{20} = +55°$ (c=0.5% in benzene):.

Various modifications of the products and process of the invention may be made without departing from the spirit or scope thereof and it is to be understood that the invention is intended to be limited only as defined in the appended claims.

What we claim is:

1. A process for the preparation of 1R, cis compounds in all their possible isomeric forms of the formula

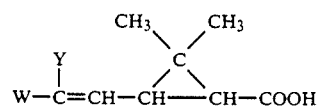

wherein W is hydrogen when Y is —COOR' or —COSR' and W is halogen when Y is —COOR' and R' is selected from the group consisting of (1) hydrogen, tert.-butyl, —CH₂OCH₃, benzyl and —CH₂—SCH₃ with the double bond having Z configuration when W is hydrogen and the E configuration when W is halogen comprising reacting the lactone of cis 2,2-dimethyl-3-dihydroxymethyl-cyclopropane-1-carboxylic acid in the presence of a strong base with a phosphorane of the formula

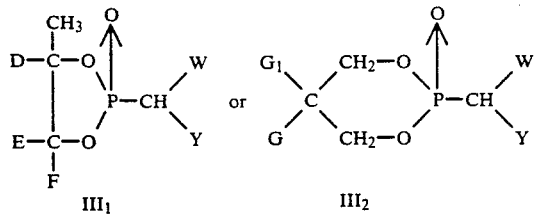

III₁      III₂ wherein C, D, E, F, G AND G₁ are selected from the group consisting of hydrogen and alkyl of 1 to 3 carbon atoms to obtain the corresponding compound of formula I with the cyclopropane and carboxy of Y both being in the 1R cis position with respect to the double bond.

2. The process of claim 1 wherein C and E are hydrogen and D and F are methyl.

3. The process of claim 1 wherein the reaction is effected at $-10°$ to $+25°$ C.

4. The process of claim 1 wherein the reaction is effected on a solvent selected from the group consisting of tetrahydrofuran, dimethylformamide, dimethylsulfoxide, hexamethylphosphoretriamide and dimethoxyethane and mixtures thereof with aliphatic or aromatic hydrocarbons.

5. A process of claim 1 wherein the compound of formula III has the formula

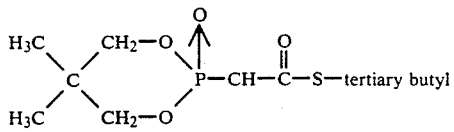

to obtain a compound of the formula

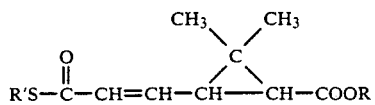

wherein the double bond has the Z configuration.

* * * * *